United States Patent [19]

Loeb et al.

[11] Patent Number: 5,601,617
[45] Date of Patent: Feb. 11, 1997

[54] MULTICHANNEL COCHLEAR PROSTHESIS WITH FLEXIBLE CONTROL OF STIMULUS WAVEFORMS

[75] Inventors: Gerald E. Loeb; Michael A. Faltys, both of Northridge, Calif.

[73] Assignee: Advanced Bionics Corporation, Sylmar, Calif.

[21] Appl. No.: 429,749

[22] Filed: Apr. 26, 1995

[51] Int. Cl.$^6$ ............................. A61N 1/36; H04R 25/00
[52] U.S. Cl. .............................................. 607/56; 607/57
[58] Field of Search .................................. 607/55, 56, 57, 607/60

[56] References Cited

U.S. PATENT DOCUMENTS

| | | | |
|---|---|---|---|
| 4,267,410 | 5/1981 | Forster et al. | 607/57 |
| 4,408,608 | 10/1983 | Daly et al. | 607/60 |
| 4,515,158 | 5/1985 | Patrick et al. | 607/57 |
| 4,532,930 | 8/1985 | Crosby et al. | 607/57 |
| 4,612,934 | 9/1986 | Borkan | 607/57 |
| 5,095,904 | 3/1992 | Seligman et al. | 607/57 |

*Primary Examiner*—William E. Kamm
*Assistant Examiner*—Carl H. Layno
*Attorney, Agent, or Firm*—Fitch, Even, Tabin & Flannery

[57] ABSTRACT

A method and system of readily specifying a wide range of temporospatial patterns of electrical stimulation waveforms that can be used by an implantable cochlear prosthesis. Such stimulation patterns and waveforms can thus be readily tested by an audiologist in the process of fitting the cochlear prosthesis, allowing desirable patterns of pulsatile stimuli of almost arbitrary complexity to be modulated in real-time by the acoustic signal to produce useful perceptions of sound in otherwise deaf patients. The cochlear prosthesis includes two main components: (1) an external system, and (2) an implantable system. The external system includes electronic circuitry, typically including a microprocessor, that converts sensed acoustical signals to electrical signals and processes the electrical signals in accordance with a desired speech processing strategy. The present invention facilitates the definition of complex stimulation waveforms to be used as part of the selected speech processing strategy. In a preferred embodiment, the stimulation patterns and waveforms are specified in a template table, the rows and columns of which define time intervals and stimulation sites. Alternatively, the stimulation patterns and waveforms may be specified in a list of spatial/temporal events.

25 Claims, 13 Drawing Sheets

Simple Biphasic CIS

| TIME | C1 | C2 | C3 | C4 | C5 | C6 | C7 | C8 | C9 |
|------|----|----|----|----|----|----|----|----|----|
| t0   | -1 |    |    |    |    |    |    | 0  | D  |
| t1   | 1  |    |    |    |    |    |    |    |    |
| t2   | 0  | -1 |    |    |    |    |    |    |    |
| t3   |    | 1  |    |    |    |    |    |    |    |
| t4   |    | 0  | -1 |    |    |    |    |    |    |
| t5   |    |    | 1  |    |    |    |    |    |    |
| t6   |    |    | 0  | -1 |    |    |    |    |    |
| t7   |    |    |    | 1  |    |    |    |    |    |
| t8   |    |    |    | 0  | -1 |    |    |    |    |
| t9   |    |    |    |    | 1  |    |    |    |    |
| t10  |    |    |    |    | 0  | -1 |    |    |    |
| t11  |    |    |    |    |    | 1  |    |    |    |
| t12  |    |    |    |    |    | 0  | -1 |    |    |
| t13  |    |    |    |    |    |    | 1  |    |    |
| t14  |    |    |    |    |    |    | 0  | -1 |    |
| t15  |    |    |    |    |    |    |    | 1  |    |

Simultaneous Pulses on two or more Channels for Double-Speed CIS

| TIME | C1 | C2 | C3 | C4 | C5 | C6 | C7 | C8 | C9 |
|------|----|----|----|----|----|----|----|----|----|
| t0   | -1 |    |    | 0  | -1 |    |    | 0  | D  |
| t1   | 1  |    |    |    | 1  |    |    |    |    |
| t2   | 0  |    |    |    | 0  |    |    |    |    |
| t3   |    | -1 |    |    |    | -1 |    |    |    |
| t4   |    | 1  |    |    |    | 1  |    |    |    |
| t5   |    | 0  |    |    |    | 0  |    |    |    |
| t6   |    |    | -1 |    |    |    | -1 |    |    |
| t7   |    |    | 1  |    |    |    | 1  |    |    |
| t8   |    |    | 0  |    |    |    | 0  |    |    |
| t9   |    |    |    | -1 |    |    |    | -1 |    |
| t10  |    |    |    | 1  |    |    |    | 1  |    |

MULTICHANNEL COCHLEAR PROSTHESIS WITH FLEXIBLE CONTROL OF STIMULUS WAVEFORMS

BACKGROUND OF THE INVENTION

The present invention relates to multichannel cochlear prosthesis, and more particularly to a multichannel cochlear prosthesis that offers flexible control of the stimulus waveforms.

Cochlear prostheses produce sensations of sound in deaf patients by direct electrical stimulation of the auditory nerve. In modern, multichannel cochlear prostheses, several different sites are stimulated at various distances along the cochlea to evoke the different pitches of sound perception that are normally encoded by nerve activity originating from the respective sites. The patterns of electrical stimulation are derived from acoustic signals picked up by a microphone and transformed by a so-called speech processor that is programmed to meet the particular requirements of each patient. Several different schemes for processing the acoustic signal and transforming it into electrical stimuli have been developed and are well-described in the scientific literature and various patents. All of these schemes can be divided into two basic types on the basis of the waveforms of the electrical stimuli:

i) Analog waveforms, which are essentially filtered versions of the continuous acoustic waveform, usually involving dynamic range compression, bandpass filtering and scaling to the stimulus current ranges that evoke a satisfactory range of auditory sensations from threshold of perception to maximal comfortable loudness. This produces a rich but poorly controlled set of resultant waveforms.

ii) Biphasic pulses, which consist of a single cycle of a square wave in which current flows in one direction at a specified magnitude and for a specified brief period of time and is followed immediately by an opposite direction of current of a similar magnitude and duration. These pulses are most often delivered in sequence to various sites, with the instantaneous magnitude at each site proportional to some measure of the amount of energy present in a particular frequency band of the acoustic waveform. The result is an impoverished but precisely controlled set of stimulus waveforms.

Both of these stimulus waveform types have been selected because they are relatively easy to produce and modulate electronically for real-time encoding of speech and because they guarantee a charge-balanced alternating current at the electrodes, avoiding net direct current that is known to cause electrolytic damage to both electrodes and body tissues.

Recent findings regarding the complex biophysical phenomena associated with the electrical excitation of neurons and psychophysical phenomena regarding the interpretation of neural activity by the auditory nervous system suggest that the quality and intelligibility of speech percepts evoked by a cochlear prosthesis may be improved in a given patient by more specific manipulations of the electrical stimulus waveforms tailored to that patient. In particular, more complex sequences of polarities, with or without pauses between phases and sites, and with or without simultaneous current delivery at more than one site, appear to be desirable. There is thus a need in the art for a cochlear stimulation system that allows complex stimulation waveforms to be individually tailored for each stimulation site.

SUMMARY OF THE INVENTION

The present invention provides a method and/or system whereby a rich set of temporospatial patterns of electrical stimulation can be tested by an audiologist in the process of fitting the cochlear prosthesis, and in which desirable patterns of pulsatile stimuli of almost arbitrary complexity can be modulated in real-time by the acoustic signal to produce useful perceptions of sound in otherwise deaf patients.

In order to implement the present invention, a cochlear stimulation system is required. Such cochlear system includes two main components: (1) a wearable or external system, and (2) an implantable system. The wearable (external) system includes a speech processor coupled to a headpiece. The speech processor includes a battery, or equivalent power source, and further includes electronic circuitry, typically including a microprocessor, that converts sensed acoustical signals to electrical signals and processes the electrical signals in accordance with a desired speech processing strategy. It is a feature of the present invention to facilitate the definition of complex stimulation waveforms to be used as part of the selected speech processing strategy, thereby enhancing the ability of the system to produce useful perceptions of sound for a deaf patient.

The headpiece, which is typically adapted to be worn by a patient in or behind the ear, includes a microphone for sensing the acoustical signals and converting them to electrical signals, and further includes an antenna, or coil, for transmitting the processed signals to, and receiving signals from, the implantable system.

The implantable system is adapted to be implanted so that it can readily receive signals from, and (in some embodiments) send signals to, the externally-worn headpiece. Typically, the implantable system, frequently referred to as an implantable cochlear stimulator (ICS), contains no power source, but rather receives its operating power from the signals that are coupled or transmitted to it from the wearable system. However, it is to be emphasized that the present invention is not limited to an ICS that is powered only from the external system, but applies to any implantable stimulation system that is controlled by an external system.

The implantable system or ICS employs a multiplicity of electrical current sources, each connected to at least one unique electrode contact within the cochlea. Electronic circuitry is also included in the implantable system that permits the sign (polarity) and magnitude of the output current of each of the current sources to be electronically re-specified at frequent, predetermined intervals.

In operation, the speech processor defines or specifies the complex stimulation waveforms that are to be used by the ICS, and transmits such definition/specification to the ICS at frequent, predetermined intervals. The ICS responds by generating such complex stimulation waveforms at the times, and for the durations, indicated in the received definition/specification, and then applying such generated waveforms to designated tissue locations, i.e., to specific electrode contacts that are positioned within the cochlea (or other living tissue).

In accordance with one aspect of the invention, a template of the desired temporal sequence of output currents from the various current sources within the ICS is stored digitally within the speech processor as a table of weighting coefficients (or weighting factors) whose columns (or rows) represent the different current sources of the ICS, and whose rows (or columns) represent intervals of time. Such table may also contain additional columns that control other aspects of the stimulation, such as the actual duration of the time interval represented by each row. The template thus consists of a modest number of intervals (typically 20–100) whose total duration defines a "cycle" of stimulation. At the beginning of each new stimulation cycle, information derived from the acoustical signal during the previous cycle is used to compute the magnitude of stimulation required for each of the current sources of the ICS during the new cycle. In each successive interval of the new cycle, the instantaneous current flow to be generated from each of the current sources during the new cycle is determined by multiplying the magnitude of stimulation by the corresponding weighting factor that is stored in the table. Such information is transferred to the ICS during each interval of the new cycle, where it is acted upon by the electronic circuitry within the ICS to generate the specified instantaneous current flow at the appropriate time.

The present invention may thus be broadly characterized as a cochlear prosthesis system that includes: (1) an implantable cochlear stimulator (ICS); (2) a wearable processor (WP); and (3) means for powering and controlling the ICS from the WP. In such system the ICS includes a multiplicity of electrode pairs and means for generating a multiplicity of temporospatial patterns of controlled stimulus waveforms that are applied to said electrode pairs as controlled by said WP. Advantageously, the WP allows the patterns of controlled stimulus waveforms to be defined easily, such that the stimulus waveforms applied to each electrode pair can be individually controlled and specified with minimal intrusion into the basic operation of the WP.

It is thus a feature of the present invention to facilitate the definition/specification of a wide range of different temporospatial patterns of electrical stimulation current that can be generated by an implantable cochlear stimulator.

It is another feature of the invention to allow complex stimulation waveforms to be defined/specified in a simple manner.

It is yet an additional feature of the invention, in accordance with one aspect thereof, to allow the definition/specification of the stimulation current to be created simply by writing appropriate numbers into a table that defines a current stimulation template, with the rows/columns of the table defining time and electrode pairs (which, electrode pairs, once implanted, define specific stimulation locations within the cochlea). Thus, the intersection of a given row and column of the table simply specifies the magnitude, polarity, and time during which the specified stimulation current is applied to a given electrode pair (stimulation location).

It is a further feature of the invention to allow the cycles of stimulation information that are sent to an implanted stimulator to be selectively shortened so that the stimulation information may be updated at a more rapid rate.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

The present invention relates to a method and system for permitting a wide variety of complex stimulation patterns and waveforms to be used by a multi-channel implantable cochlear stimulator. A preferred multi-channel cochlear stimulator of the type that may be used by the invention is described in U.S. patent application Ser. No. 08/322,065, filed Oct. 12, 1994, which patent application is incorporated herein by reference. It is to be understood, however, that the invention is not limited to use only by the type of stimulator described in the cited patent application, but may be used with any multi-channel cochlear stimulator that includes the ability to set a prescribed stimulation current for each channel of the stimulator.

Figure 1:
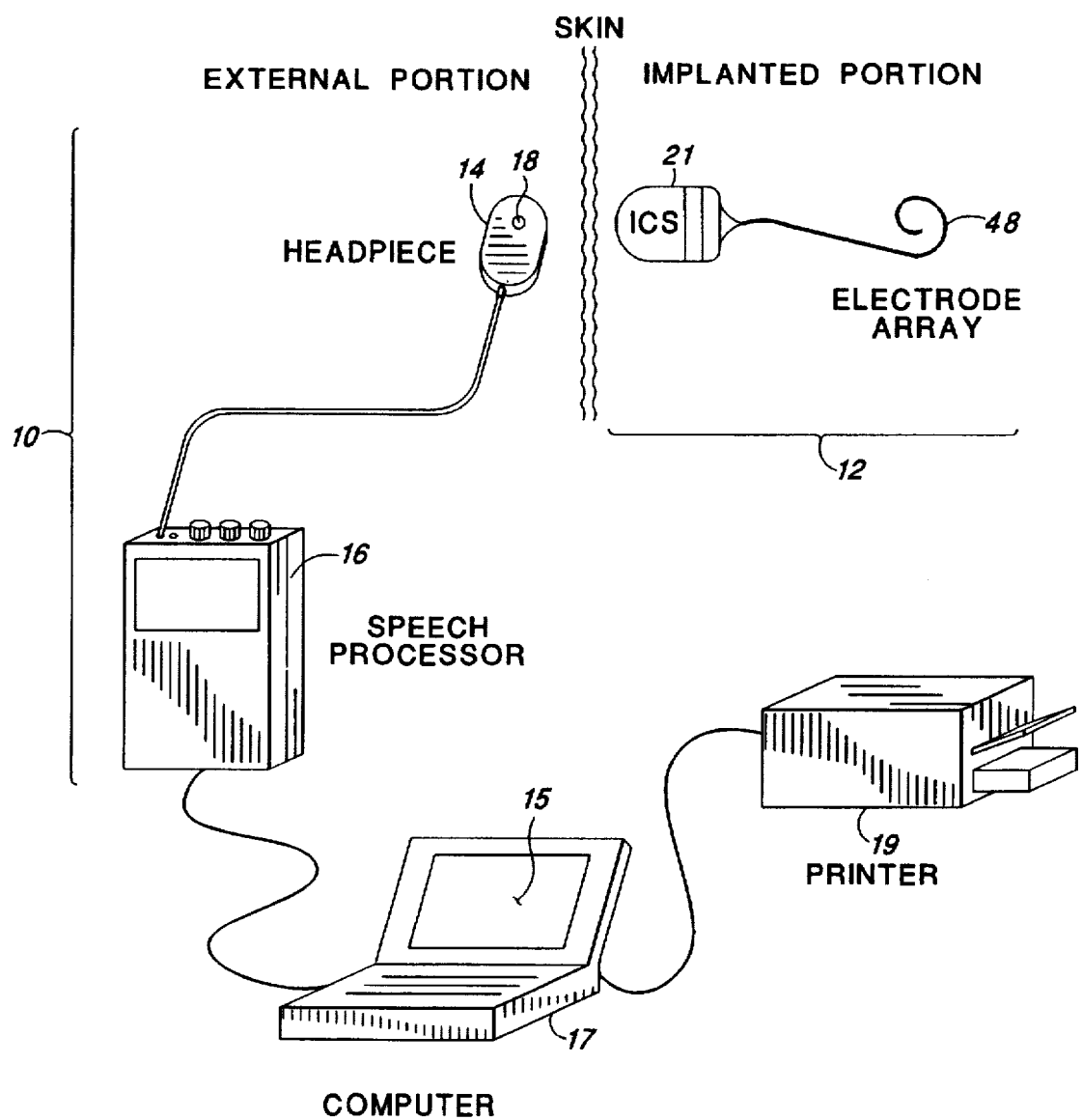
FIG. 1 shows the main elements of a cochlear stimulation system.

Turning to FIG. 1, there is shown a cochlear stimulation system that includes an external portion 10 and an implantable portion 12. The external portion includes a speech processor 16 (which may also be referred to as a wearable processor 16), and a headpiece 14. The implantable portion includes an implantable cochlear stimulator (ICS) 21, and an electrode array 48. The electrode array 48 is adapted to be inserted within the cochlea of a patient. The array 48 includes a multiplicity of electrodes spaced along its length that are selectively connected to the ICS 21. The electrode array 48 may be substantially as shown and described in U.S. Pat. No. 4,819,647, incorporated herein by reference. Electronic circuitry within the ICS 21 allows a specified stimulation current to be applied to selected pairs or groups of the individual electrodes included within the electrode array 48 in accordance with a specified stimulation pattern, defined by the speech processor 16.

The ICS 21 and the headpiece 14 each include an antenna coil. In operation, i.e., when the ICS has been implanted and the headpiece 14 is positioned to be aligned over the location where the ICS is implanted, such coils are inductively coupled to each other, thereby allowing information (e.g., the magnitude and polarity of a stimulation current) and power to be transmitted from the speech processor 16 to the ICS 21. Some models of the ICS 21 also permit information to be transmitted from the ICS 21 back to the speech processor 16.

The headpiece 14 also includes a microphone 18 that senses acoustic signals and converts such sensed signals to corresponding electrical signals. The speech processor 16 processes these converted acoustic signals in accordance with a specified speech processing strategy in order to generate appropriate control signals for controlling the ICS. Such control signals specify or define the polarity, magnitude, location (which electrode pair receives the stimulation current), and timing (when the stimulation current is applied to the electrode pair) of the stimulation current that is generated by the ICS.

It is common in the cochlear stimulator art to condition the magnitude and polarity of the stimulation current applied to the implanted electrodes in accordance with a specified stimulation strategy. Such stimulation strategy involves defining a pattern of stimulation currents and waveforms that are to be applied to the electrodes. For example, it is common to apply a biphasic stimulation pulse to a given electrode pair, having a magnitude that varies as a function of the sensed acoustic signal. (A "biphasic" pulse is generally considered as two pulses: a first pulse of one polarity having a specified magnitude, followed immediately, or after a very short delay, by a second pulse of the opposite polarity having the same magnitude.) If multiple electrode pairs exist, as is the case with a multi-channel cochlear stimulator, then it is also common to sample the acoustic signal at a rapid rate, and apply a biphasic stimulation pulse in sequence to each of the pairs of electrodes in accordance with a specified pattern and cycle time, with the magnitude of the stimulation current being a function of information contained within the sensed acoustic signal at a given (e.g., the most recent) sample time.

Heretofore, all known stimulation systems have been severely limited in their ability to specify more than one or two stimulation patterns for use with the implantable stimulator. Moreover, what patterns have been available have been limited to very simple stimulation waveforms, e.g., sequencing through each electrode pair in a fixed sequence with simple biphasic pulses of varying amplitude, or sequencing through each electrode pair in a fixed sequence with simple biphasic pulses of varying width. There are no known cochlear stimulation systems that permit complex stimulation waveforms to be individually tailored for each stimulation site (where each "stimulation site" corresponds to a selected electrode pair). The present invention advantageously overcomes this limitation by providing an almost infinite variety of complex stimulation waveforms that can be easily specified and thereafter used by the implantable stimulator. Such flexibility in defining or specifying the stimulation patterns thus allows the audiologist, or other medical personnel who is fitting the implantable unit, to readily customize the stimulation patterns and waveforms used by the stimulation system to be optimized for a particular patient.

Still referring to FIG. 1, it is seen that a laptop computer 17, or other type of computer, or equivalent device, may be coupled to the speech processor 16 in accordance with the present invention. Such laptop computer 17 (or equivalent device) provides a display screen 15 on which stimulation templates and other information may be displayed and defined. Such computer 17 thus provides a very simple way for the audiologist or other medical personnel, or even the patient, to easily specify a particular pattern of stimulation waveforms that may be thereafter used, even if for just a short testing period, regardless of whether such stimulation pattern is simple or complex. Also shown in FIG. 1 is a printer 19 which may be connected to the computer 17 if desired in order to allow a record of the stimulation templates and pattern(s) that have been specified to be printed.

Figure 2:
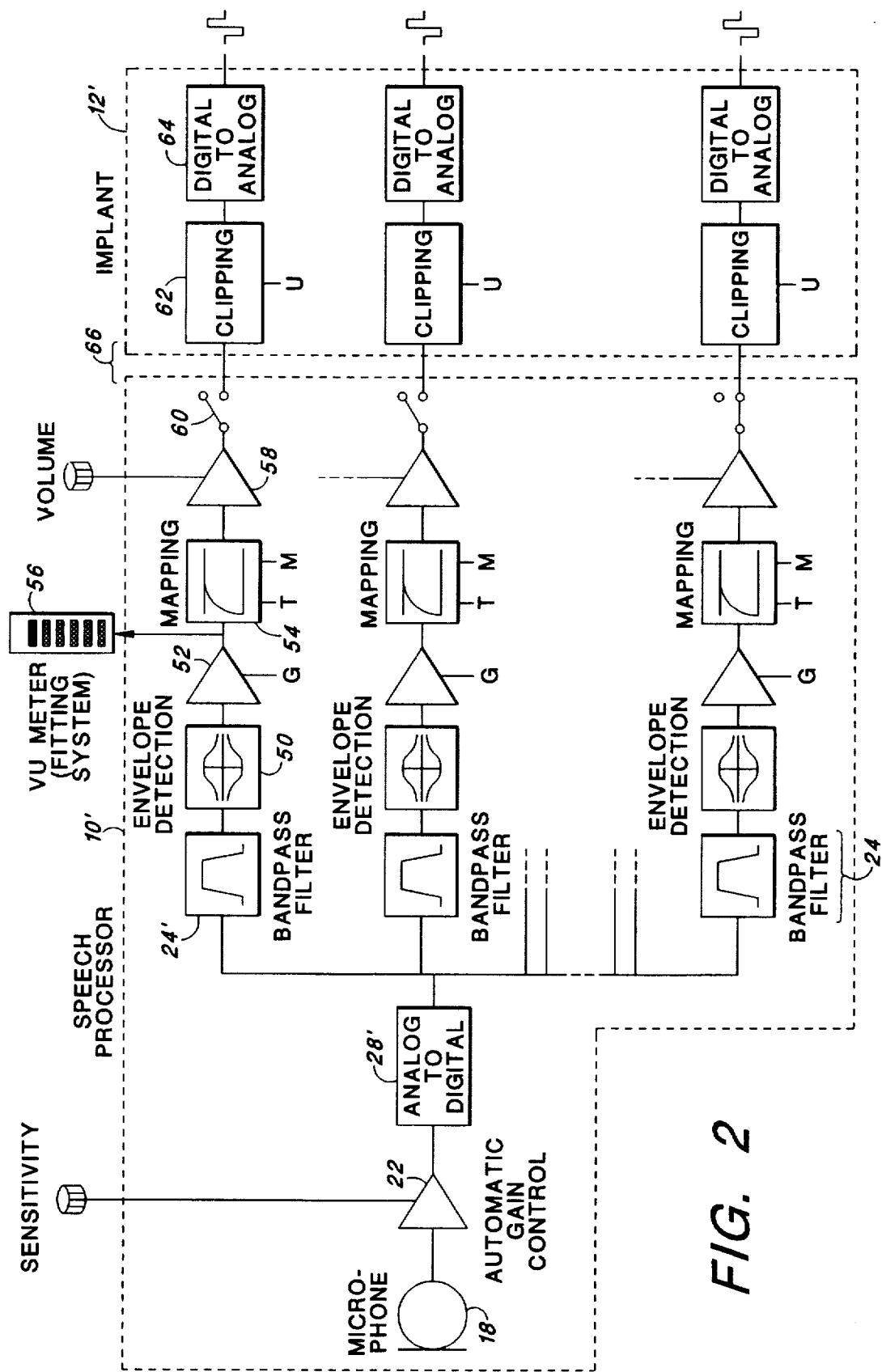
FIG. 2 is a partial functional block diagram of the wearable and implantable portions of the system of FIG. 1.

Turning next to FIG. 2, a partial functional block diagram of the external or wearable portion 10' and the implantable portion 12' of the stimulation system of FIG. 1 is shown. It is to be emphasized that what is shown in FIG. 2 depicts the functions that are carried out by either the external portion 10' or the implantable portion 12'. The actual electronic circuitry that is used to carry out these functions is not critical to the present invention, although a representation of a preferred embodiment of such circuitry is shown below in FIG. 3 and in the cited patent application. It should also be pointed out that the particular functions shown in FIG. 2 are representative of just one type of signal processing strategy that may be employed (relating to dividing the incoming signal into frequency bands, and independently processing each band). Other signal processing strategies could just as easily be used to process the incoming acoustical signal, and the present invention could still be used to provide added flexibility in specifying the stimulation patterns and waveforms that are used.

In FIG. 2, it is seen that the external portion 18 includes a microphone 18 to sense acoustical information and convert it to electrical signals. These signals are then amplified in audio front-end circuitry 22, which includes an amplifier having automatic gain control, and typically also includes a manual "sensitivity" control. The amplified audio signal is then converted to a digital signal by analog to digital (A/D) converter 28'. The resulting digital signal is then processed in one of a multiplicity of digital signal processing channels. For example, eight separate channels may be used, each responding to a different frequency content of the sensed acoustical signal. That is, the incoming signal is divided into a multiplicity of frequency channels, as defined by respective bandpass filters included within a filter bank 24.

Except for the frequency band of the individual filters 24' each of the channels into which the incoming signal is divided are virtually identical. Hence, only one such channel will be described herein. After passing through its respective bandpass filter 24', the envelope of the resulting signal is detected using envelope detection circuitry 50. This signal is then amplified by amplifier 52. A VU meter 56 may then be used to graphically display the amount of signal energy present within the band. The signal is then mapped to an appropriate magnitude, using mapping circuitry 54, depending upon its frequency content, with lower frequency signals within the band being attenuated more than higher frequency signals. A final amplification stage 58 sets the volume of the signal, and the signal is then passed over to the implantable portion 12' through a switch 60 and a telemetry channel 66.

The implantable portion 12' once it receives the signal, limits its amplitude to a safe value with a clipping circuit 62, converts the signal back to an analog signal using digital to analog (D/A) converter 64, and then applies the analog signal to the electrodes that have been configured for the appropriate channel.

Those of skill in the art will recognize that the above description of FIG. 2 is significantly simplified. For example, the telemetry channel 66 typically requires that the information form each channel be reformatted into a serial data stream, or data frame, that is passed serially over to the implantable portion 12' through inductively coupled coils. Once received within the implantable portion, such data frame must be processed in an appropriate manner to recover the information for each channel and present such recovered information to the respective electrode pair for that channel. Such telemetry channel details, while interesting, are not really critical to an understanding of the present invention, except as indicated below.

Further, it is noted that the manner in which the switches 60 are operated plays a significant role in defining the particular speech processing strategy that is employed by the system. For example, if the switches 60 are operated such that only one switch is closed at any instant of time, but at a rapid rate, then the external portion 10' of the stimulation system effectively samples the incoming acoustical signal, one frequency band at a time. Such a strategy, which stimulates only one electrode pair or cochlear location at any instant of time, is known as a "continuous interleaved sampler" (CIS) strategy. In contrast, if the switches 60 are operated such that they are always closed, then the information in that frequency channel is effectively processed continuously. Such a strategy, which may stimulate more or all of the electrode pairs with a respective stimulation waveform at the same time, is known as a "continuous analog" (CA) strategy. In one sense, the present invention may be viewed as a method or technique for controlling the switches 60 of each channel so as to provide much more flexibility in the type of stimulation strategy employed by the implantable portion 12' of the stimulation system.

Figure 3:
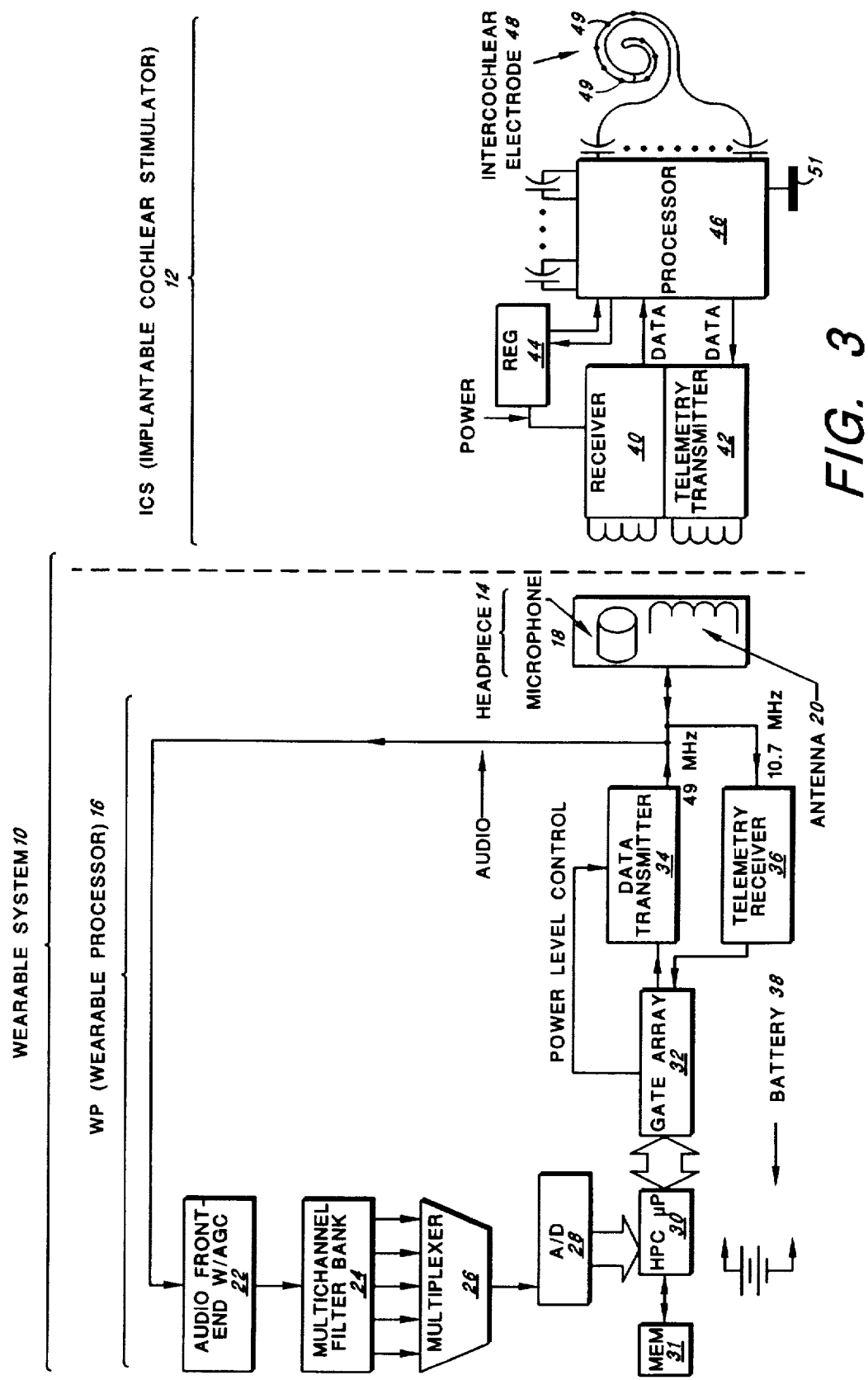
FIG. 3 shows a block diagram of the wearable and implantable portions of the system of FIG. 1 in accordance with a preferred embodiment thereof.

Referring next to FIG. 3, a block diagram of a preferred embodiment of the system of FIG. 1 is shown. Such preferred embodiment is described fully in the above-referenced patent application. Basically, the preferred embodiment shown in FIG. 3 comprises an externally wearable system 10 and an implantable cochlear stimulator (ICS) 12. The external system 10 comprises a headpiece 14 and an externally wearable processor (WP) 16. The headpiece may be worn behind the ear of a hearing impaired person and comprises a conventional microphone 18 and an antenna (coil) 20 for transmitting and receiving electromagnetic energy in the form of radio frequency signals or inductively coupled high frequency signals. Such coupling can be restricted to magnetic field coupling only by an electrostatic shield around the coils comprising the antenna 20. In addition, signals from the ICS to the WP on one carrier frequency and from the WP to the ICS on another frequency can be transferred via a single coaxial cable between the headpiece 14 and the WP 16. This can be accomplished by having tuned inductor-capacitor filters for each frequency at each end of the coaxial cable.

The WP 16, powered by a battery 38, is adapted to receive audio signals received by the microphone 18 and to transmit such signals to a conventional audio front end 22 which features automatic gain control (AGC). The audio signals processed by the audio front end 22 are transmitted to a bank of filters 24 for filtering and for generation of a plurality of parallel audio signals. The audio signals are processed by a multiplexer 26 and converted to a series of digital signals by an A/D converter 28 for application to a microprocessor 30. The filter bank may also be implemented as a group of digital filters, for example in a digital signal processor integrated circuit. In this case the signal flow would be from the audio front end and AGC 22, through an antialiasing filter, to an analog to digital converter, then into a digital filter bank 24 and the general processing of microprocessor 30.

The output of the microprocessor 30 is coupled through a custom gate array 32 that converts data from the microprocessor into a serial bit stream going to a data transmitter 34. The gate array 32 also converts data from a telemetry receiver 36 and the microprocessor 30 to control the power level of and data generated by the data transmitter 34.

As illustrated in FIG. 3, the ICS 12 includes a receiver 40 for receiving data transmissions from the wearable system 10 and a telemetry transmitter 42 for transmitting ICS status indicating and measured signals from the ICS 12 to the wearable system 10 for processing thereby. For example, power level indicating signals transmitted by the telemetry transmitter 42 are received by the telemetry transmitter 36 and processed in the microprocessor 30 and gate array 32 to generate signals controlling the power level of the transmissions from the transmitter 34 to the ICS 12, thereby providing a closed-loop system for optimizing the power levels of the transmission from the wearable system 10 to the ICS 12 and hence conserving the battery 38 and optimizing the voltages generated within the system 10.

In addition to the receiver 40 and transmitter 42, the ICS 12 includes a regulator 44 for receiving a power signal from the receiver 40 to energize a processor 46. Data signals from the receiver 40 are also transmitted to the processor 46 for processing to generate stimulation signals applied to one or more of a plurality of capacitor coupled electrodes 49 in an intracochlear electrode 48. The preferred embodiment of the invention provides eight channels, each of which includes two electrodes which may be paired together in order to provide bipolar stimulation. Alternatively, the channels may be configured for monopolar stimulation where a selected one of the two electrodes of the channel is paired with a common reference electrode 51.

Generally speaking, in response to control or data signals from the WP 16 the processor 46 selectively monitors voltages of the electrodes and associated circuitry in the processor and generates ICS status indicating and measured signals. For example, the processor 46 monitors the voltage applied to the regulator 44, the impedance of the electrodes and other voltages within the processor to generate the status indicating signals which are sent as data to the wearable telemetry transmitter 42 for transmission to the wearable system 10.

More particularly, in the cochlea stimulating system shown in FIG. 3, the signals transmitted to the ICS 12 from the wearable system 10 include electrical power components. Such power components are processed within the receiver 40 through the series regulator 44 to generate a voltage signal which powers the processor 46. The processor 46 selectively monitors the voltage applied to the series regulator and generates a status indicating signal relative to such voltage which is transmitted by the telemetry transmitter 42 and received by the telemetry receiver 36. As previously stated, such information is utilized in the microprocessor 30 and gate array 32 of the WP 16 to control the power level of the transmissions from the data transmitter 34 to the ICS 12.

Figure 4:
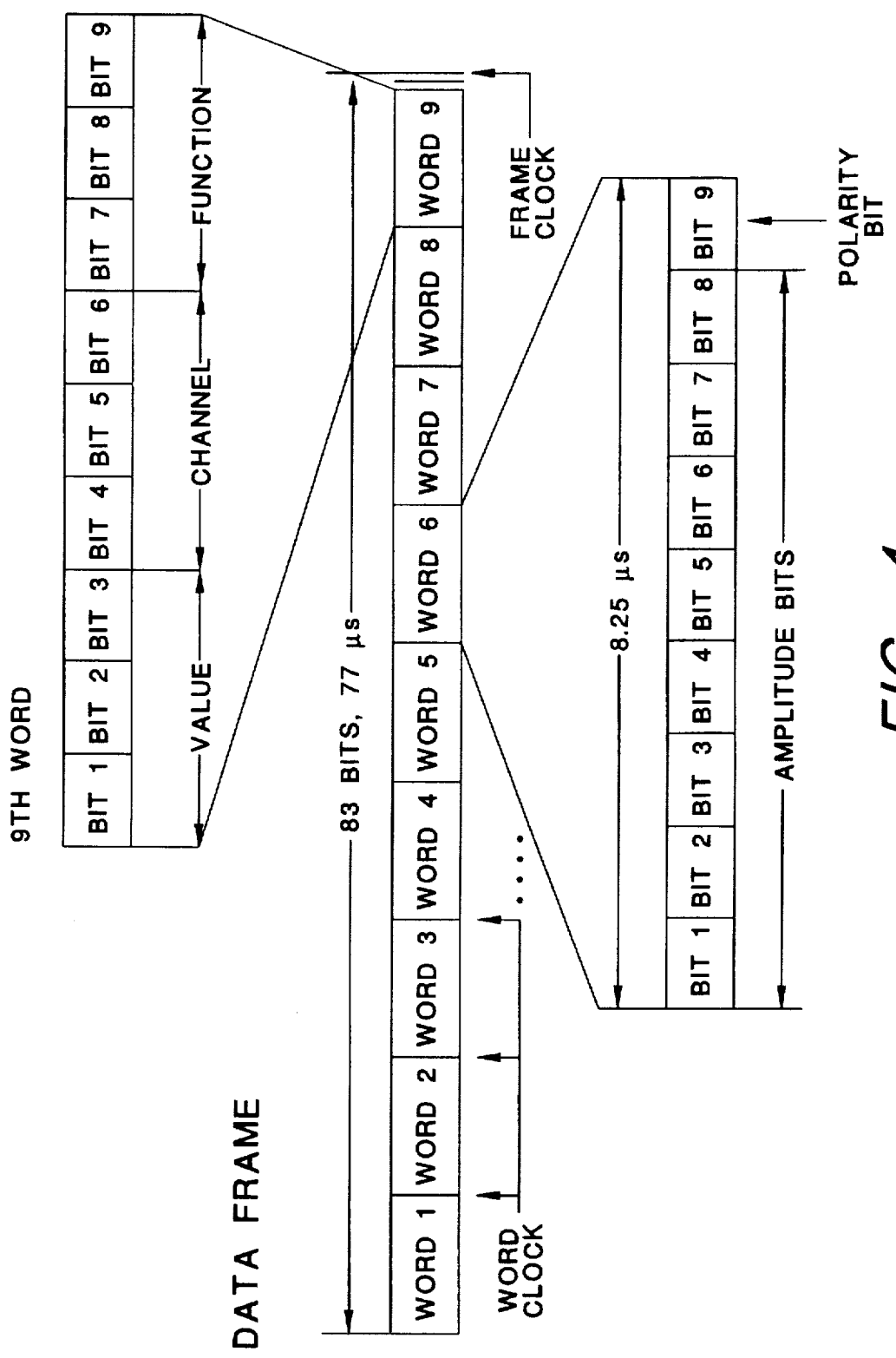
FIG. 4 shows the makeup of a data frame used with the preferred system of FIG. 3.

Turning next to FIG. 4, there is shown the makeup of a typical data frame used with the preferred system of FIG. 3. Such data frame is necessary due to the fact that multiple channels of stimulation information are needed by the ICS 12, yet there is only a single telecommunications channel through which information may be transferred to the ICS. In other words, use of the data frame shown in FIG. 4 allows parallel data channels to be temporarily reformatted into a serial data channel to facilitate transmission of the information to the ICS.

As seen in FIG. 4, the typical data frame is made up of 9 nine-bit words, plus a parity bit and an end-of-frame bit, or a total of 83 bits. The clock rate is such that the overall duration of a complete data frame is about 77 μsec.

The first eight words in the data frame are data words, and each contains amplitude bits (the first eight bits) and a polarity bit. Each data word corresponds to the stimulation information for a given channel. The last word of the data frame, or the ninth word, is a control word. Such word is used to control and/or set various functions within the ICS, e.g., the electrode configuration (bipolar or monopolar) that the ICS will use. The general format of the control word is also shown in FIG. 4.

Figure 5:
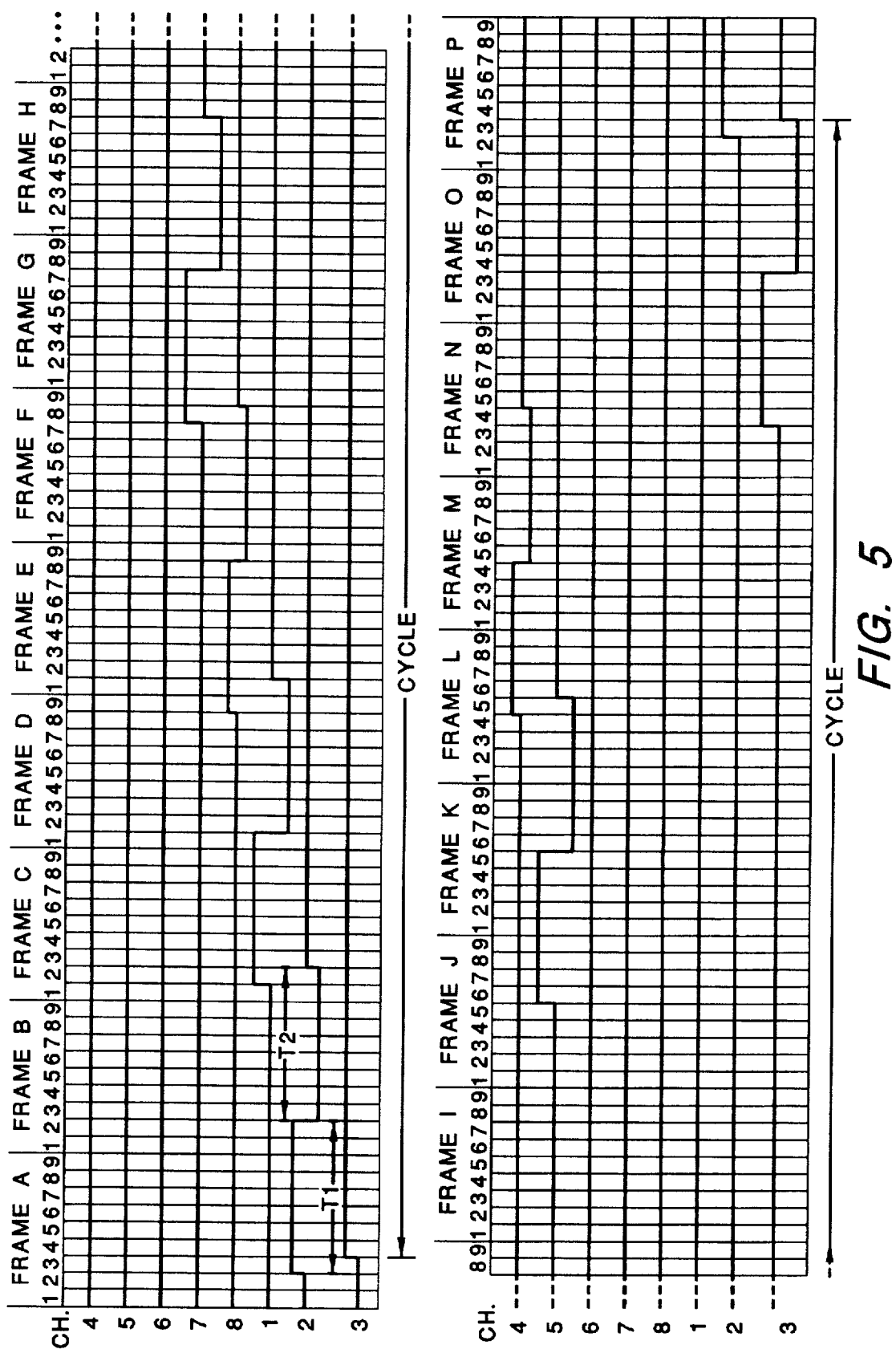
FIG. 5 illustrates how multiple data frames are used with the system of FIG. 3 in order to achieve a desired stimulation pattern that repeats itself in cycles.

FIG. 5 illustrates how multiple data frames may be used with the system of FIG. 3 to achieve a desired stimulation pattern that repeats itself in cycles. The particular stimulation pattern shown in FIG. 3 approximates a simple CIS strategy because, for the most part, only one electrode pair (channel) is stimulated with a biphasic pulse at any given time. To understand FIG. 5, it is important to recognize that the data word in each data frame specifies the amplitude and polarity for the stimulation current of the corresponding channel. Such amplitude and polarity, once set by a data words, remains unchanged until a new data word, in a new data frame, is received to a change. Thus, to make produce a biphasic stimulation pulse, it is necessary to specify an amplitude and polarity for the channel in a first data frame, specify the amplitude and opposite polarity in a second data frame, and finally, specify a zero amplitude in a third data frame. If a CIS strategy is employed, as approximated in FIG. 5, then each channel is maintained at a zero amplitude until such time in the cycle as it is that channel's turn to be stimulated in the specified sequence.

As shown in FIG. 5, for example, the specified sequence comprises (starting at the left of the figure) stimulating the electrode pair of channel 2, then channel 1, then channel 8, then channel 7, then channel 6, then channel 5, then channel 4, and then channel 3. In a first data frame, Frame A, a positive stimulation current is applied to the electrodes of channel 2. The magnitude of this stimulation current is a function of the sensed acoustic signal falling within the frequency band corresponding to channel 2, and as otherwise processed by the speech processor 16. Note that during data Frame A, not only is channel 2 stimulated, but the stimulation current already present in channel 3 is turned off. This process continues, as shown, with each phase of the biphasic pulse lasting for a time equal to the length of a data frame, and with the complete stimulation cycle requiring 16 data frames.

Still referring to FIG. 5, the numbers 1–9 included for each data frame correspond to the nine data words present in each data frame. Thus, when a change is included in the first word of the data frame, such change occurs early in the data frame, whereas a change that occurs in the last word of the data frame, occurs late in the data frame. Given this restriction, one aspect of the present invention relates to mapping the particular electrode pair associated with the words of the data frame so that the electrode pair in contact with the basal end of the cochlea, which receives high frequency information and thus has the most information capacity, is mapped to the first word in the data frame. The apex of the cochlea, which receives low frequency information and thus has the least information capacity, is mapped to the last word in the data frame. This mapping scheme, in combination with sending partial frames (as described below) advantageously permits a two-to-three times faster update rate to occur at the base of the cochlea than has heretofore been possible.

It should be noted that the stimulation pattern depicted in FIG. 5 represents a simple (non-complex) stimulation pattern. The present invention advantageously utilizes simple and easy-to-define stimulation templates that permit the ICS to generate much more complex stimulation patterns without having to significantly alter the basic operating programs of the speech processor 16, and without having to alter the circuitry of the ICS 12. In fact, the stimulation templates of the present invention may advantageously be used with any type of stimulation system that provides an implanted stimulator that follows the commands of an external processor in a master/slave relationship. That is, so long as the individual channels (or specific tissue stimulation locations as defined by a selected electrode pair) of the implanted stimulator can be set to a specific stimulation current value (including a zero value) as controlled by the external processor, and remain at those values until reset by the external processor to a new stimulation current value, then the present invention can advantageously be used by such system.

Figure 6:
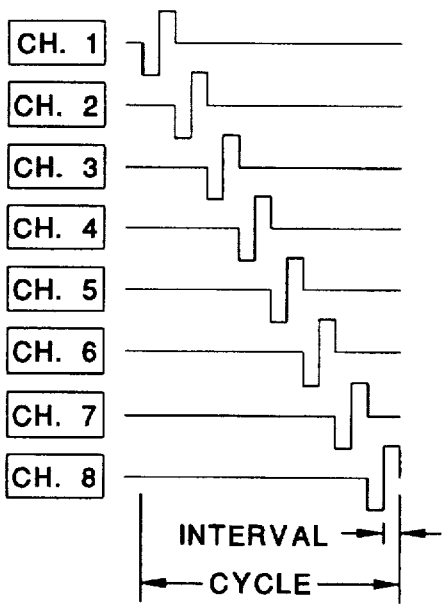
FIG. 6 illustrates a simple biphasic CIS stimulation template for use with the present invention that provides a CIS stimulation pattern for an eight-channel stimulator device.

To illustrate, FIG. 6 shows one representation of a simple biphasic CIS stimulation template for use with the present invention that provides a CIS stimulation pattern for an eight-channel stimulator device. The template is in the form of a stimulation table, shown on the right side of FIG. 6. The biphasic stimulation currents that result from using such template are represented on the left side of FIG. 6. Note that the stimulation table or template comprises rows and columns. Each row represents an increment of time, which increment of time may be set to an appropriate value for the particular application. For the table shown in FIG. 6, it is presumed that all of the increments of time, t0–t15, are equal increments of time. However, as will be demonstrated by other possible templates shown below, the time increments need not be equal, but can be specified to any appropriate value.

Each column of the template table shown in FIG. 6 represents a channel, or stimulation location, Thus, referring to FIG. 6 it is seen that each cell (i.e., each intersection of a row and column) of the template table defines a particular stimulation current that is to be applied to a specific location (the channel, or column) at a particular time (the specified time, or row). The combination of all the cells of the template table thus defines a particular temporospatial stimulation pattern, or a particular cycle of stimulation waveforms, that are to be applied to specific stimulation locations at specific times within the stimulation cycle.

The numerical values inserted into the cells of the template table represent weighting factors which are to be used to modify the amplitude of the processed signals (derived from the incoming acoustical signal). A null value (blank) table cell specifies a zero stimulus waveform for the channel and time specified by the column/row of the template. Typically, the weighting factor will simply be used as a multiplication factor. Thus, if the template table contains a "+1" in a given cell, then that means the processed signal for that channel is to be multiplied by a "+1", with the product of such multiplication serving to define or specify the amplitude of the desired stimulation current to be applied to the electrode pair of the channel at the indicated time increment.

It is to be emphasized that the rows and columns of the template table can be reversed and the template table will still serve its intended function of clearly and easily defining a particular stimulation pattern, even a complex stimulation pattern (as is demonstrated below) for use by an ICS or equivalent stimulator device. That is to say, each column of the table may represent an increment of time, and each row of the table may represent a channel, or stimulation location.

Referring to FIG. 6, it is seen that at time t0, the first channel, C1, has a value "−1" inserted therein. All other cells in the table at time t0 are blank (null values), except for C8 (which has a "0" inserted therein), and C9 (which has a "D" inserted therein). The "−1" in the cell corresponding to channel C1 at time t0 means that whatever magnitude is present in the channel 1 signal at time t0 will be multiplied by a "−1". The "0" simply means that channel C8 is to be reset back to zero (null) at time t0. The "D" in channel C9 (which is the control word channel) means that the ninth work command is to be set to its default value. At time t1, the weighting factor for channel C1 changes to a "+1". At time t2, the weighting factor for channel C1 is set to "0" and the weighting factor for channel C2 is set to "−1". The timing associated with the actual waveforms for the stimulation currents thus take the form as illustrated on the left side of FIG. 6.

Figure 7:
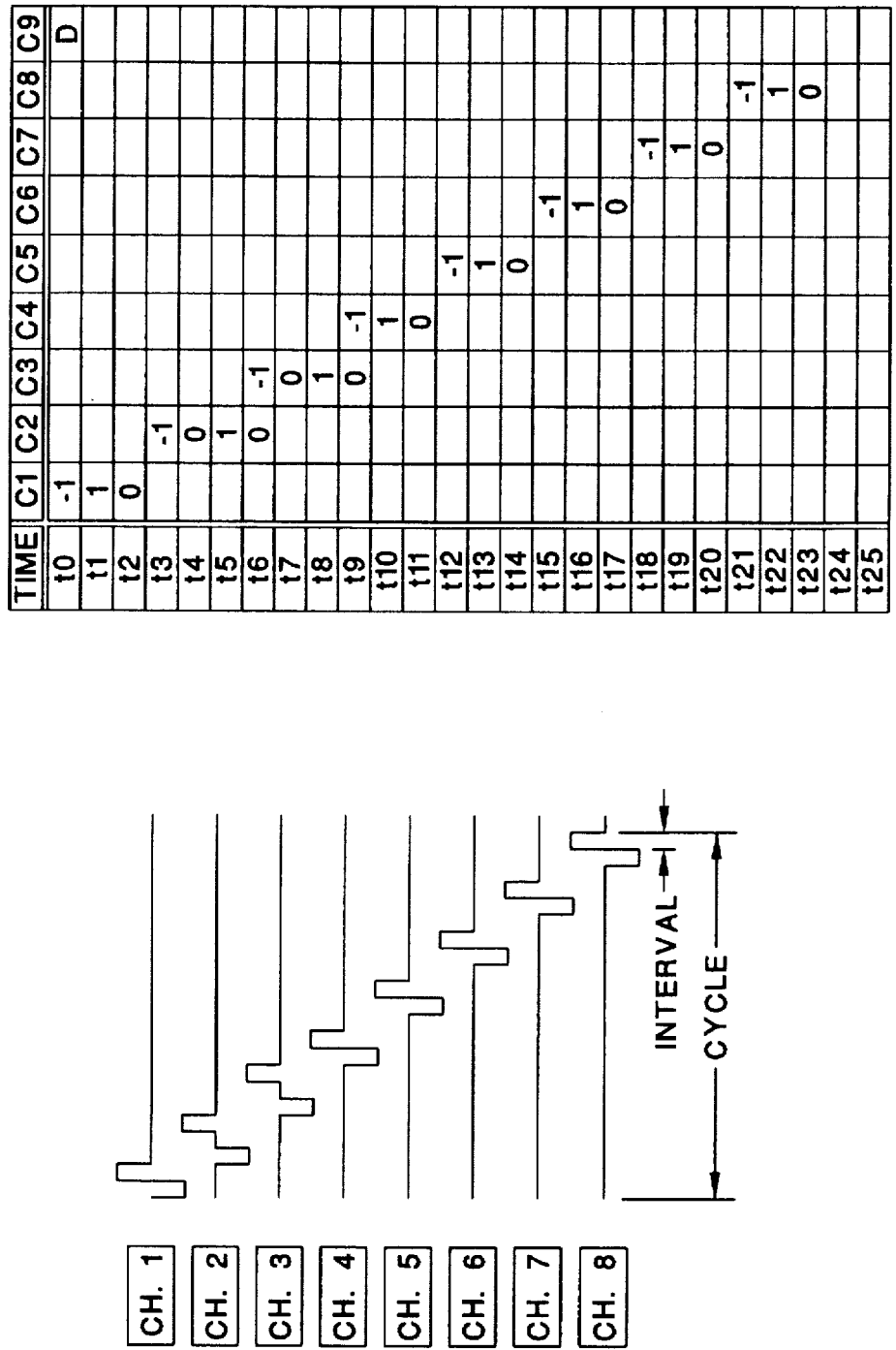
FIG. 7 shows the stimulation template for a somewhat more complex biphasic stimulation pattern that includes time delays between phases and channels.

FIG. 7 shows the stimulation template table as in FIG. 6, but for a somewhat more complex biphasic stimulation pattern that includes time delays between phases and channels.

Figure 8:
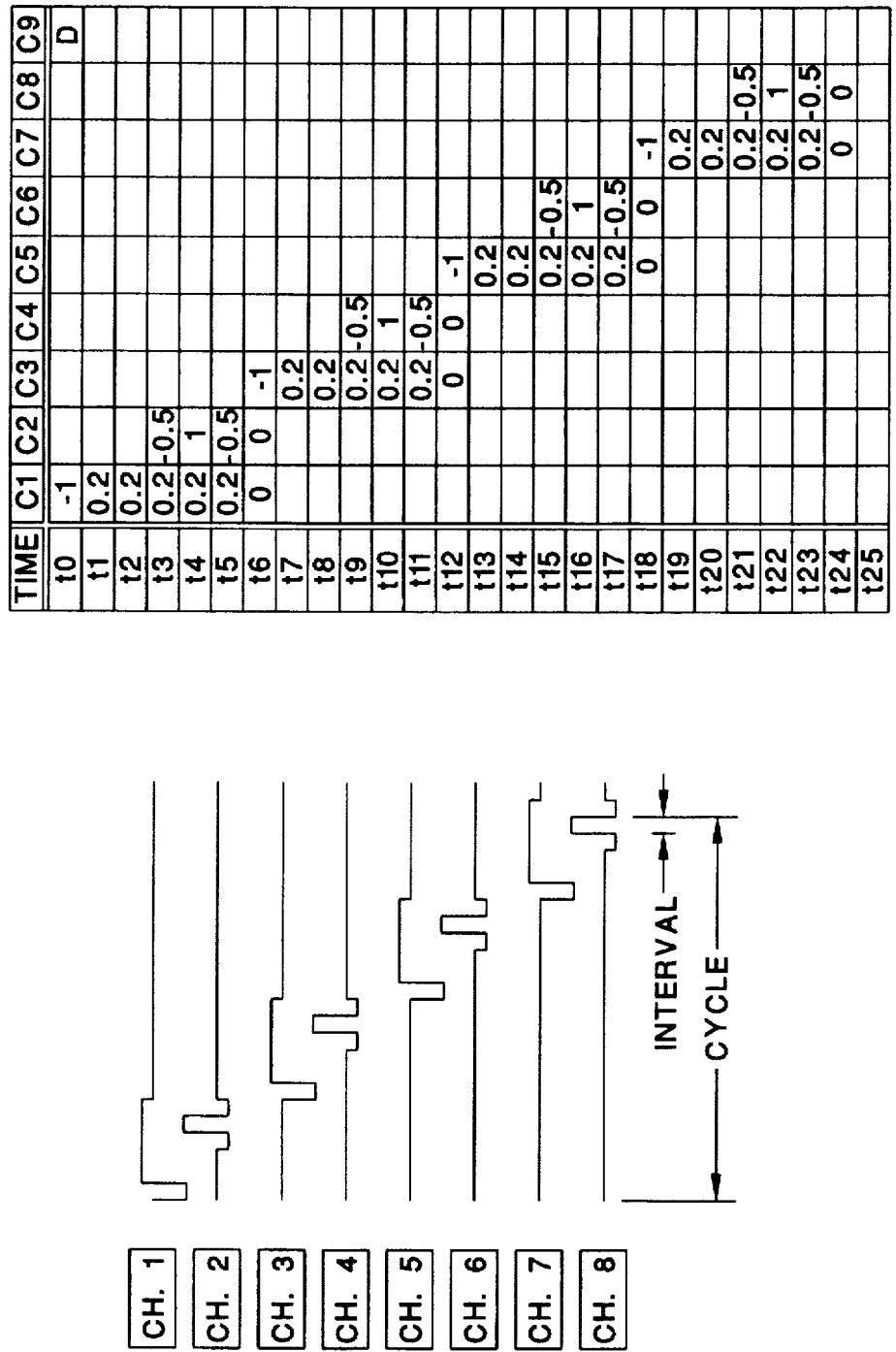
FIG. 8 depicts the stimulation template for a much more complex stimulation pattern that includes asymmetrical and triphasic pulses.

Similarly, FIG. 8 depicts the stimulation template table for a much more complex stimulation pattern that includes asymmetrical and triphasic pulses. Note that the weighting factors are selected so that the sum of the positive factors always equals the sum of the negative factors, thereby assuring a charge balance in the stimulation waveform that is ultimately generated.

Figure 9:
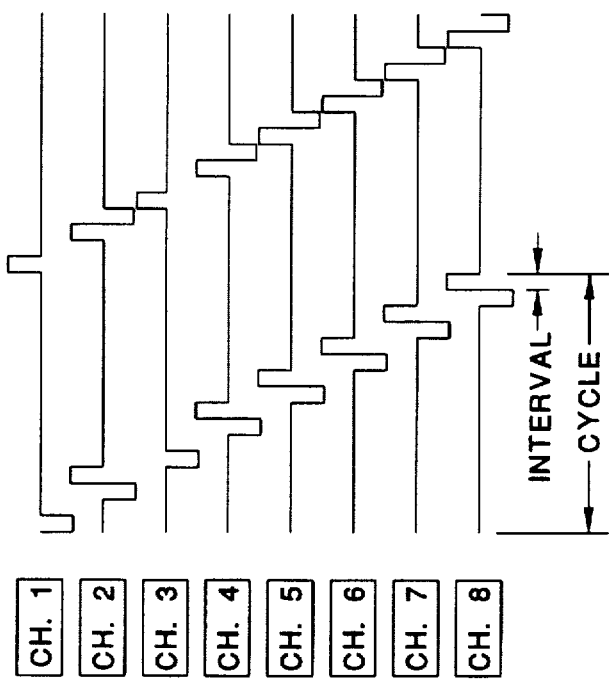
FIG. 9 shows the stimulation template for a stimulation pattern that includes alterphasic pulses.

FIG. 9 shows the stimulation template table for a stimulation pattern that includes alterphasic pulses. An alterphasic pulse is a pulse as shown for channel C1 and channel C3—a pulse of one polarity followed in the next cycle by a pulse of the opposite polarity.

It is thus seen that the numbers written into the cells of the template table allow diverse and complex patterns to be specified. Such patterns can easily be produced in real-time by a microprocessor that is programmed to read the cells of the table as input data. Because the possible output states are entirely specified by the template table, there is no possibility of unexpected delays occurring during real-time execution of the program. This is a critical feature, because the charge-balance of the waveforms produced by each current source depends on computing the weighting coefficients or factors such that the sum of the products of each weighting coefficient times the respective time interval for that row of the template table adds to zero for all weighting coefficients in each column. That is, the amount of time that each of the current sources stays in any particular output state must be predictable and reproducible from cycle to cycle.

As should be evident from an examination of the template tables presented above (and below), the length of a given row represents the length or duration of a data frame. The length of a data frame, in turn, specifies the minimum pulse width that may be included within a biphasic stimulation pulse (or other stimulation waveform). One advantage of the present invention is that means are included within the speech processor for shortening selected rows of the table in order to reduce the number of blank cells in a given row. Such shortening, in turn, thereby reduces the minimum pulse width that may be utilized in the stimulus waveform, thereby allowing a more rapid rate of pulses in the stimulus waveform. When such pulses are applied to the basal electrodes of the cochlea, it is thus possible to convey more information to the cochlea than has previously been possible.

Figure 10:
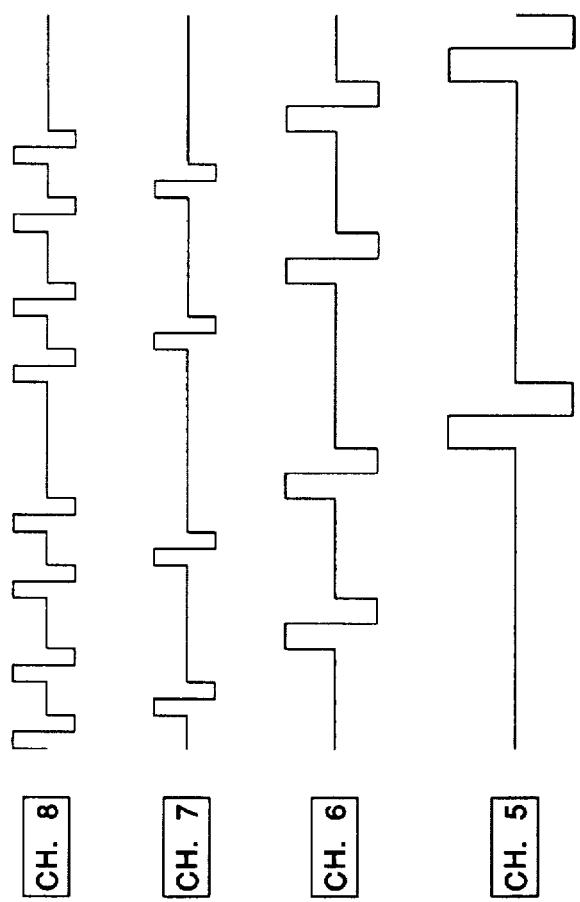
FIG. 10 illustrates the stimulation template for a stimulation pattern that includes more frequent narrow biphasic stimulation pulses in some channels, and less frequent wider biphasic stimulation pulses in other channels.

Referring next to FIG. 10, a stimulation template is illustrated for a stimulation pattern that includes more frequent narrow biphasic stimulation pulses in some channels, and less frequent wider biphasic stimulation pulses in other channels. Also note that only four of the stimulation channels are used in the pattern shown in FIG. 10: channels C5, C6, C7 and C8. In use, the C8 channel, which has the most frequent pulses applied thereto, preferably corresponds to the electrode pair placed at the basal end of the cochlea. This is because, as previously indicated, the basal end of the cochlea receives high frequency information and thus has the most information capacity. The time intervals used in FIG. 10 may be much shorter than the time intervals used, e.g., in the templates of FIGS. 6–9, so that the overall cycle length in FIG. 10 need not be any longer than, and may even be shorter than, the cycle lengths in FIGS. 6–9.

Figure 11:
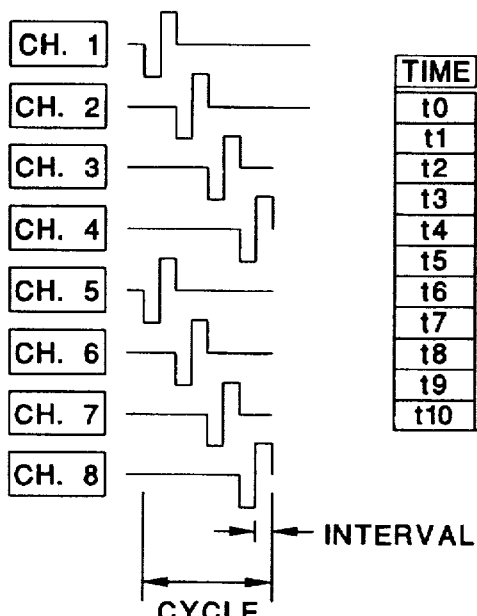
FIG. 11 depicts the stimulation template for a stimulation pattern that provides simultaneous biphasic pulses on two or more channels.

FIG. 11 depicts a stimulation template for a stimulation pattern that provides simultaneous biphasic pulses on two or more channels. Such a pattern allows the overall cycle length to be decreased significantly. The stimulation pattern shown in FIG. 11 is of particular interest because of the delivery of pulses more or less simultaneously at two or more different sites. Note that the CIS strategy is designed to minimize electrotonic interactions between the stimulus currents applied at adjacent sites by delivering brief stimulation pulses in a sequential, interleaved, i.e. non–overlapping manner. It is also desirable, however, to complete the stimulation of all sites in as short a frame time as possible, permitting the information from the acoustic signal to be sampled and presented at a relatively high rate. In order to sequence through a large number of stimulation sites at a relatively rapid rate, the length of time available to deliver each individual stimulation pulse must be made very short. The efficacy of a given stimulus pulse in activating neurons depends on the product of the magnitude and duration of the current, i.e. the total charge delivered in each phase of the waveform. In order to activate neurons with a very brief current pulse, the magnitude of the current must be made very high. Because the electrode contacts and surrounding tissue represent a significant impedance to the flow of electrical current, the applied voltage and dissipated power will also be much higher. The problem is even worse for biphasic stimulus pulses shorter than about 60–80 microseconds because the reverse polarity of the second phase partially cancels the effects of the first phase before the neurons can respond to the first phase.

Advantageously, as shown in FIG. 11, the CIS frame rate for a given number of channels each with a given pulse width can be doubled by stimulating two separate sites at the same time. This violation of the non–overlap requirement for the CIS strategy is useful only if the amount of electrotonic interaction between those sites is minimal. That condition is likely to be met when the simultaneously activated sites are selected to be physically distant from each other and when the intensity of stimulation required to produce a full range of loudness at each site is fairly low. Thus, it is a particular advantage of this invention that the pattern of overlap between pulses at various sites can be readily selected and changed simply by altering the values in the template table rather than reprogramming a new algorithm for each stimulus paradigm.

Referring next to FIG. 12, there is shown the stimulation template for a stimulation pattern that uses short–interval transmissions to create narrow pulses and a faster overall cycle rate. The time intervals used in FIG. 12 are not equal. Rather, t0 is shorter than t1, which is shorter than t2, and so on. Further, as depicted in FIG. 12, as the weighting factors decrease with increasing time intervals, the time intervals lengthen.

In the preferred embodiment, various additional codes and features can be added to the template table to provide for greater efficiency in performing the computations required for each successive interval of the frame. For example, in FIG. 12 it is seen that an "S" is inserted into the two cells preceding a stimulation of a given channel. Such "S" represents a shorting of the electrodes of that channel. The savings in computation may be used to save power consumed by the device, e.g., by causing the microprocessor to go into idle mode whenever possible. Other codes and features provide additional options regarding the duration of each phase of electrical stimulation according to the programmability of the implanted circuitry that generates the output currents.

From the above figures, it is seen that a great deal of flexibility may be achieved relative to the stimulation patterns and waveforms that are implemented by the ICS or equivalent stimulator device. For the particular embodiment of the ICS described in the referenced patent application, the following codes and features are supported, as an example of the capabilities of the general scheme of the invention:

First, the output current of each current source remains at a given value unless and until it is explicitly set to a new value, so a special "null" code in the table indicates that no change is required during a particular interval, obviating the need to recompute the output current during a phase of stimulation that lasts longer than one interval or when the desired output is zero for more than one interval.

Second, if a row of the table contains no non-null codes after a given column, then a special "end" code in the table can be used to signal that no further computations are required in that interval.

Third, if a row of the table contains no non-null codes after a given column, then a special "short interval" code in the table can be used to abridge the normal transmission of information to the implanted electronics and immediately beginning transmitting the output states specified by the next row in the table, resulting in a shorter-than-normal interval for the output states specified in the abbreviated row.

Fourth, if the table contains an extra column for mode control of the implanted electronics, the mode value stored in the template table for each row can be transmitted to the implanted electronics at each interval. Such mode values can, for example, specify that the output current that is requested of one or more of the current sources in the subsequent interval be delayed in its onset or terminated prematurely during the course of that interval, thus creating stimulus phases whose duration is a fraction of the interval represented by each row of the table.

It should be pointed out that the template table used by the present invention is a tool to facilitate abstraction of the desired stimulation pattern and waveforms. Other tools that achieve the same end result may also be used. For example, a list or series specification of desired spatial/temporal events may be mathematically or logically defined, and such list may then be used as input data to the microprocessor used within the speech processor. For example, the stimulation pattern and waveforms defined by the template table shown in FIG. 12 may alternately be generated by the following series:

$C_n$(t,amplitude): (2*(n−1),−1),(2*(n−1)+1,1),(2*(n−1)+2, 0)

$F_t$(n,code): (INT(t/2)+2,S)

where t=step number (t0–t15) or frame number;

n=channel number [1–9] or position in frame;

code=[S]hort, [D]efault, . . . all possible codes.

Figure 13:
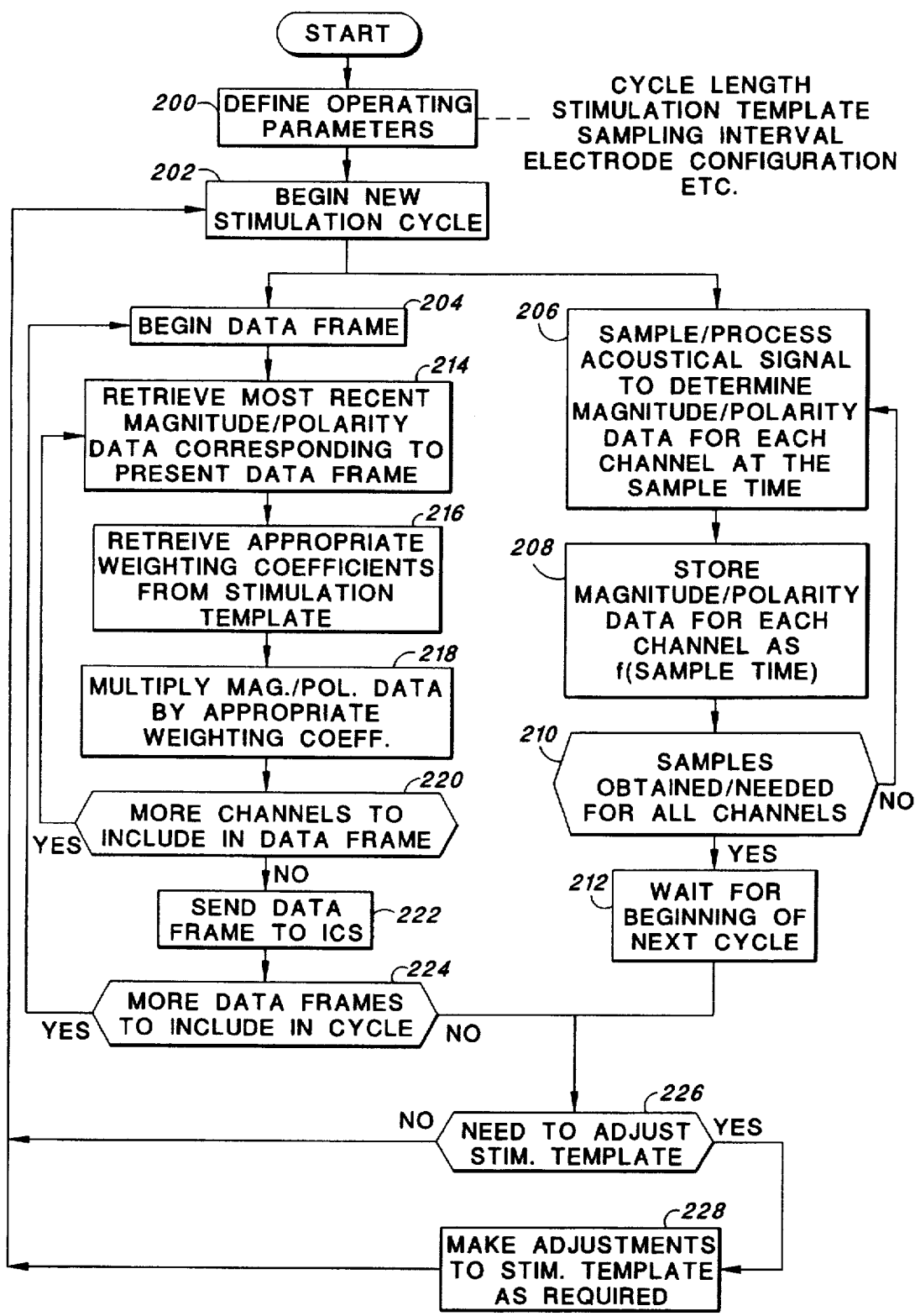
FIG. 13 is a simplified flow chart that shows how the above or other stimulation templates may be used within the external (wearable) portion of the invention to control the stimulation current patterns generated by the implantable stimulator portion of the invention.

Referring next to FIG. 13, a simplified flow chart is shown that depicts one method (certainly not the only method) by which the above or other stimulation templates may be used within the external (wearable) portion of the stimulator system to control the stimulation current patterns and waveforms generated by the implantable portion of the invention. Each main step of the method depicted in FIG. 13 is represented as a "block", where each block has a reference numeral assigned thereto.

As seen in FIG. 13, an initial step (block 200) is to define the appropriate operating parameters used by the microprocessor 30 (FIG. 3) within the external (wearable) processor 16. Such operating parameters may include such items as: the data frame interval (the time interval separating the rows in the template table), the cycle length (the number of rows in the template table), the number of channels to be used (the number of columns in the table), the electrode configuration (bipolar, monopolar, etc.), and the like.

Once the initial operating parameters are defined, a new stimulation cycle begins (block 202). As the new stimulation cycle begins, two parallel paths are initiated. In a first path, the acoustic signal is sampled and processed (block 206). Such processing results in a determination of the magnitude and polarity associated with each channel at the sample time. For the preferred ICS described herein, such processing results in generating the eight data words that make up a data frame. This magnitude/polarity information is then stored as a function of the sample time (block 208). Once such magnitude/polarity data has been obtained for each of the available channels (block 210), then this branch of the stimulation cycle waits for the beginning of the next cycle (block 212), at which time a new sample is taken and the process repeats (blocks 206, 208, 210, 212) .

Meanwhile, in the parallel path initiated at the beginning of the stimulation cycle, the data frame is initiated. This is accomplished by retrieving the most recent magnitude/polarity data corresponding to the first channel to be included in the data frame (block 214). Once this data has been retrieved, the appropriate weighting factors or weighting coefficients corresponding to the first channel and time interval are also retrieved (block 216). Such retrieval of the weighting coefficients is greatly facilitated through the use of the template table or other list as described above. The magnitude/polarity data is then multiplied by the appropriate weighting coefficient (block 218) to produce weighted magnitude/polarity data. Such weighted data effectively defines the desired stimulation current for the current data frame. Accordingly, such weighted data is formatted into the data word of the frame in anticipation of sending the data frame to the ICS. If additional channel information/data is required to complete the frame data (YES branch of block 220), then such information/data is retrieved (blocks 214, 216, 218). If all of the information/data needed within the current frame has been accumulated (NO branch of block 220), then the weighted information/data is transferred to the ICS (block 222). A determination is then made as to whether additional frames are needed to complete the cycle (block 224). If so (YES branch of block 224), then the next data frame is initiated and the process repeats (blocks 204, 214, 216, 218, 220, 222, and 224).

If the cycle is complete (NO branch of block 224), i.e., if all of the data frames needed to complete the cycle have been generated, a determination may be made as to whether there is a need to adjust the stimulation template (block 226). Such determination is preferably made in cooperation with the patient, i.e., using feedback from the patient as to how well he or she is discerning certain sounds generated as part of a fitting test. If not, then the next stimulation cycle begins and the process repeats as described above (beginning at block 202).

If a need does exist for an adjustment of the stimulation template (YES branch of block 226), then such adjustment is made (block 228). Advantageously, the template table provided by the present invention, or other list of the spatial/temporal events, makes such an adjustment a very easy task. Such task may be undertaken manually, on a trial and error basis, e.g., by simply changing the weighting factors in the template table; or may be performed systematically following a prescribed adjustment algorithm.

As described above, it is thus seen that the present invention provides a multi-channel stimulation system that facilitates the definition/specification of a wide range of different temporospatial patterns of electrical stimulation current.

It is further seen that the invention allows complex stimulation waveforms to be defined/specified in a very simple manner.

While the invention herein disclosed has been described by means of specific embodiments and applications thereof, numerous modifications and variations could be made thereto by those skilled in the art without departing from the scope of the invention set forth in the claims.

What is claimed is:

1. A cochlear prosthesis system comprising:

an implantable cochlear stimulator (ICS) having a multiplicity of electrode pairs, means for receiving power and control signals, and means responsive to receiving the power and control signals for generating a multiplicity of temporospatial patterns of stimulus waveforms that are applied to said electrode pairs;

a wearable processor (WP) including means for generating the power and control signals, means for transmitting the power and control signals to the ICS, and means for specifying within the control signals a particular temporospatial pattern of stimulus waveforms for application to each of the multiplicity of electrode pairs, whereby a first electrode pair may be stimulated with a first temporospatial pattern of stimulus waveforms, a second electrode pair may be stimulated with a second temporospatial pattern of stimulus waveforms, and so on, with each of the multiplicity of electrode pairs being stimulated with a temporospatial pattern of stimulus waveforms that has been individually specified for that electrode pair;

the WP including template means for specifying a template of a temporospatial pattern of stimulus waveforms to be applied to each of the multiplicity of electrode pairs, said template means comprising means for generating a table having rows and columns, with each one of the rows or columns being associated with one of the multiplicity of electrode pairs, and with each one of the other of the columns or rows being associated with an increment of time such that a consecutive sequence of the other of the columns or rows represents increasing time, and wherein the intersection of each row and column comprises a table cell, and wherein said template means further includes means for inserting a data value in any cell of said table, said data value defining the amplitude and polarity of the stimulus waveform for the electrode pair and time represented by the table cell wherein the data value is inserted, whereby the template of the temporospatial pattern of stimulus waveforms specified for a given electrode pair is defined by the sequence of data values inserted in the column or row of said table corresponding to said given electrode pair.

2. The cohlear prosthesis system of claim 1 wherein said template means further includes means for interpreting a blank table cell as specifying a zero stimulus waveform for the electrode pair corresponding to the column of the blank table cell at the time corresponding to the row of the blank table cell.

3. The cochlear prosthesis system of claim 2 wherein the rows of the table are associated with an increment of time such that a sequence of consecutive rows represents increasing time, and wherein each column of the table is associated with one of the multiplicity of electrode pairs.

4. The cochlear prosthesis system of claim 2 wherein the columns of the table are associated with an increment of time such that a sequence of consecutive columns represents increasing time, and wherein each row of the table is associated with one of the multiplicity of electrode pairs.

5. The cochlear prosthesis system of claim 2 wherein the WP further includes means for displaying the table generated by said template means, including displaying the data values and blanks which may be inserted into the individual cells of said table.

6. The cochlear prosthesis system of claim 2 wherein the length of the row or column used to represent increasing time defines a data frame having a specified duration, which specified duration in turn defines a minimum pulse width that may be utilized in the stimulus waveform.

7. The cochlear prosthesis system of claim 6 wherein said template means includes means for shortening selected rows of said table to reduce the number of blank cells in the row, thereby reducing the minimum pulse width that may be utilized in the stimulus waveform, thereby allowing a more rapid rate of pulses in the stimulus waveform.

8. The cochlear prosthesis system of claim 7 wherein the WP includes mapping means for specifying that the pulses of the stimulus waveform having the minimum pulse width and most rapid rate are directed within the ICS to a first electrode pair positioned within the cochlea to best provide high frequency information to the cochlea.

9. The cochlear prosthesis system of claim 8 wherein the first electrode pair is positioned near a basal end of the cochlea.

10. The cochlear prosthesis system of claim 1, wherein the template means includes means for specifying a multiplicity of temporaspatial patterns of stimulus waveforms, said multiplicity of temporospatial patterns of stimulus waveforms including biphasic pulses, biphasic pulses with delays, asymmetrical pulses, and triphasic pulses.

11. The cochlear prosthesis system of claim 10 wherein the multiplicity of temporospatial patterns of stimulus waveforms further includes alterphasic pulses.

12. The cochlear prosthesis system of claim 1 further including means for stimulating a first electrode pair with a first temporospatial pattern of stimulus waveforms at the same time that a second electrode pair is stimulated with a second temporospatial pattern of stimulus waveforms.

13. The cochlear prosthesis system of claim 12 wherein the stimulation means further includes means for stimulating other electrode pairs besides the first electrode pair and the second electrode pair simultaneously at a time when the first and second electrode pairs are not stimulated.

14. The cochlear prosthesis system of claim 1 wherein the temporospatial pattern of stimulus waveforms comprises a double-speed continuous interleaved sampling (CIS) strategy wherein simultaneous pulses are applied on at least two pairs of electrodes each time a stimulus waveform is generated.

15. The cochlear prosthesis system of claim 14 wherein the simultaneous pulses that are applied on at least two pairs of electrodes each time a stimulus waveform is generated comprise biphasic stimulation pulses.

16. The cochlear prosthesis system of claim 1 wherein the temporospatial pattern of stimulus waveforms comprises a continuous interleaved sampling (CIS) strategy wherein short pulses are applied at a rapid rate to a first electrode pair, and longer pulses are applied at a less frequent rate to a second electrode pair.

17. The cochlear prosthesis system of claim 16 wherein a short pulse is applied to the first electrode pair for every two pulses included in the stimulus waveform.

18. The cochlear prosthesis system of claim 1 wherein the template means of the WP comprises means for mathematically defining the table which specifies the temporaspatial pattern of stimulus waveforms to be applied to each of the multiplicity of electrode pairs.

19. The cochlear prosthesis system of claim 1 wherein the template means of the WP comprises means for logically defining the table which specifies the temporaspatial pattern of stimulus waveforms to be applied to each of the multiplicity of electrode pairs.

20. A method of controlling an implantable cochlear stimulator (ICS), said ICS including a multiplicity of channels, each channel having a pair of stimulation electrodes associated therewith and means for generating and applying a stimulation pulse thereto; and means for defining a data frame that defines a time period during which the multiplicity of channels are stimulated in accordance with a prescribed pattern; said method comprising the steps of:

(a) specifying external to the ICS a particular type of stimulation waveform that is desired for each channel of the ICS during each data frame, said type of stimulation waveform including a specification of a stimulation pulse polarity, magnitude, duration, and time of occurrence within the data frame, the type of stimulation waveform specified for one channel being completely independent of the type of stimulation waveforms specified for others of the channels, whereby each channel has its own stimulation waveform specified therefor, which stimulation waveform need not be the same as the stimulation waveform specified for another channel, but can be when desired, said specifying comprising:

generating a table having rows and columns, each column or row being associated with one of the multiplicity of channels, and each row or column being associated with an increment of time equal to the duration of the narrowest pulse width to be included within the stimulation waveform, such that the channels and increments of time form the two ordinates of the table, with the sum of the time increments from all of the rows/columns of the table equaling the time period of a data frame, and wherein the intersection of each row and column comprises a table cell, and inserting an alphanumerical value in the cell of the table that defines the desired amplitude and polarity of the stimulus waveform for the channel and frame time corresponding to the table cell, whereby the temporospatial pattern of stimulus waveforms specified for a given channel is defined by the sequence of alphanumerical values inserted in the column/row of said table corresponding to said given channel;

(b) generating and transmitting a control signal to the ICS that defines the particular type of stimulation waveform desired for each channel of the ICS;

(c) receiving the control signal at the ICS; and (d) generating the stimulation waveform specified by the control signal for each channel of the ICS during each data frame.

21. The method of claim 20 further including interpreting a null value (blank) table cell as specifying a zero stimulus waveform for the channel corresponding to the column/row of the null value table cell at the frame time corresponding to the row/column of the null value table cell.

22. The method of claim 21 further including shortening the frame time by an amount equal to the number of cells in a given row/column of the table that contain nothing but null values.

23. A multichannel cochlear prosthesis comprising:

a speech processor;

a cochlear stimulator; and means for coupling the speech processor and the cochlear stimulator together so that data signals and control signals may be passed therebetween;

said speech processor including:

template storage means for storing a set of coefficients that represent a particular temporospatial pattern of stimulus waveforms, means responsive to the set of coefficients stored in the template storage means for generating data and control signals that specify a particular temporospatial pattern of controlled stimulus waveforms to be generated by respective channels within the cochlear stimulator; and said cochlear stimulator including:

means for receiving said data and control signals from the speech processor, a multiplicity of channels, each having at least one pair of electrodes associated therewith, means for generating a controlled stimulus waveform for each of the multiplicity of channels as a function of said data and control signals received from the speech processor, and means for applying the controlled stimulus waveform to at least two of the multiplicity of channels so that the specified controlled stimulus waveform appears across the paired electrodes of at least two channels.

24. The multichannel cochlear prosthesis of claim 23 wherein the controlled stimulus waveform applied to at least two of the multiplicity of channels comprises a waveform selected from the group comprising biphasic pulses, triphasic pulses, asymmetrical pulses, and alterphasic pulses.

25. The multichannel cochlear prosthesis of claim 23 wherein the means for applying the controlled stimulus waveform to at least two of the multiplicity of channels includes means for grouping the multiplicity of channels into a plurality of groups of channels, wherein each group includes at least two channels; and means for simultaneously applying the controlled stimulus to each of the plurality of channels in each group in sequence so that all of the channels in a first group receive the controlled stimulus at a first time, all of the channels in a second group receive a controlled stimulus at a second time, and so on, until all of the groups have received the controlled stimulus in sequence.

* * * * *

UNITED STATES PATENT AND TRADEMARK OFFICE
CERTIFICATE OF CORRECTION

PATENT NO. : 5,601,617
DATED : February 11, 1997
INVENTOR(S) : Loeb, et. al.

It is certified that error appears in the above-identified patent and that said Letters Patent is hereby corrected as shown below:

<u>IN THE DRAWINGS</u>: Delete FIG. 12B

Figure 12A:
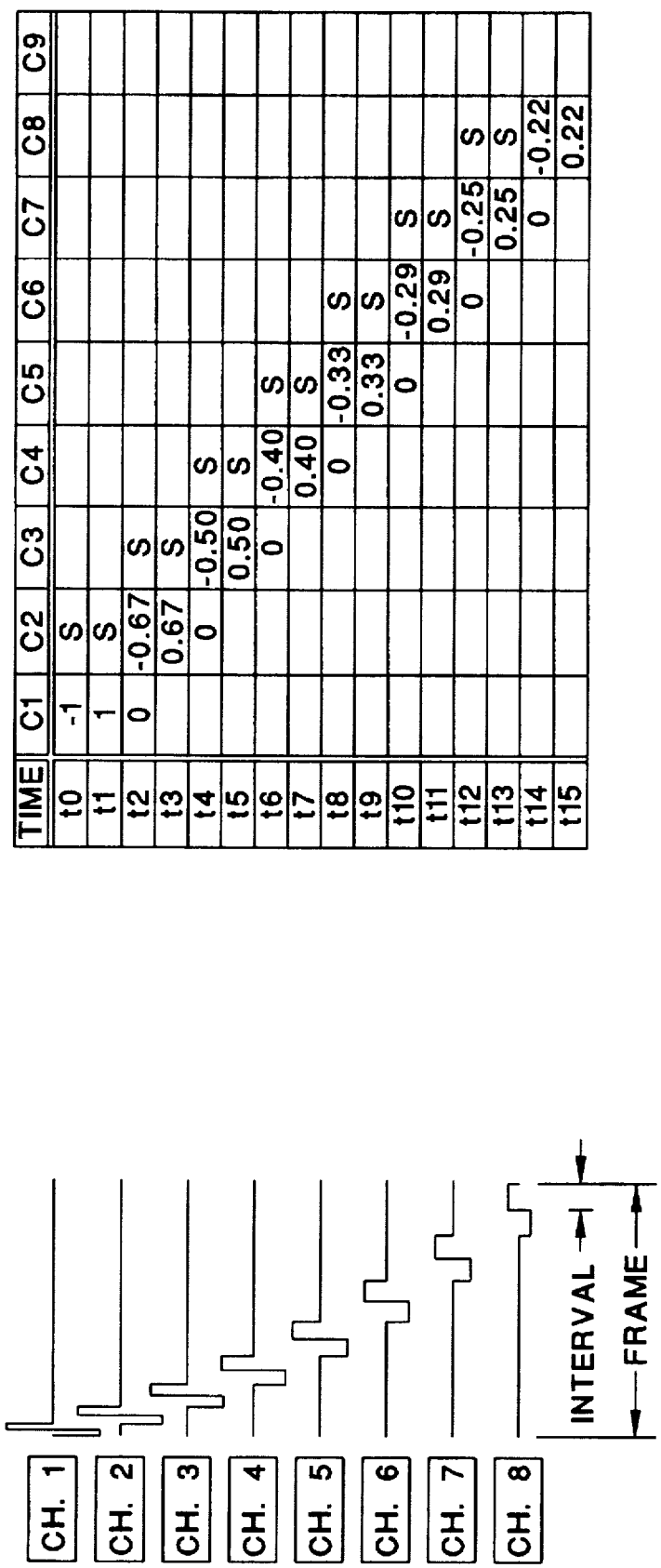
FIG. 12 shows the stimulation template for a stimulation pattern that uses short-interval transmissions to create narrow pulses and a faster overall cycle rate.
Figure 12B:
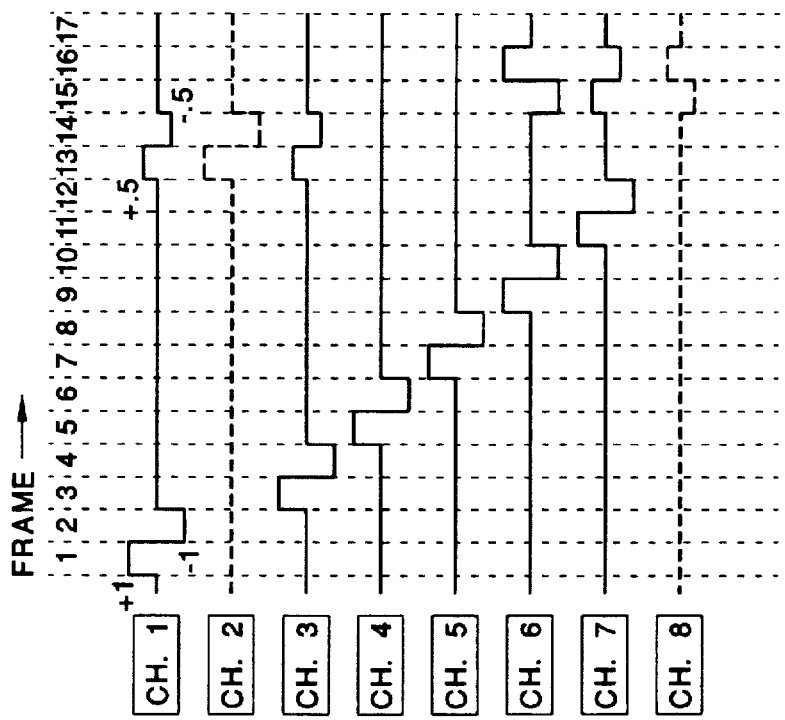

Change "FIG. 12A" to --FIG 12--.

Signed and Sealed this

Tenth Day of March, 1998

Attest:

BRUCE LEHMAN

Attesting Officer

Commissioner of Patents and Trademarks